US012674752B2

(12) United States Patent
Perelman

(10) Patent No.: US 12,674,752 B2
(45) Date of Patent: Jul. 7, 2026

(54) RAPID DETECTION AND IDENTIFICATION OF BACTERIA DIRECTLY FROM WHOLE BLOOD WITH LIGHT SCATTERING SPECTROSCOPY BASED BIOSENSOR

(71) Applicant: Beth Israel Deaconess Medical Center, Inc., Boston, MA (US)

(72) Inventor: Lev T. Perelman, Brookline, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 179 days.

(21) Appl. No.: 18/574,571

(22) PCT Filed: Jul. 1, 2022

(86) PCT No.: PCT/US2022/035960
§ 371 (c)(1),
(2) Date: Dec. 27, 2023

(87) PCT Pub. No.: WO2023/278846
PCT Pub. Date: Jan. 5, 2023

(65) Prior Publication Data
US 2024/0288367 A1 Aug. 29, 2024

Related U.S. Application Data

(60) Provisional application No. 63/218,184, filed on Jul. 2, 2021.

(51) Int. Cl.
G01N 21/51 (2006.01)
C12Q 1/04 (2006.01)
(Continued)

(52) U.S. Cl.
CPC .............. G01N 21/51 (2013.01); C12Q 1/04 (2013.01); G01N 33/49 (2013.01); *G01N 2021/4704* (2013.01); *G01N 2201/0683* (2013.01)

(58) Field of Classification Search
CPC ................... G01N 21/51; G01N 33/49; G01N 2021/4704; G01N 2201/0683; C12Q 1/04
See application file for complete search history.

(56) References Cited

U.S. PATENT DOCUMENTS

| | | | |
|---|---|---|---|
| 4,374,644 A * | 2/1983 | Armstrong | ............. G01N 33/49 436/63 |
| 2009/0047664 A1 * | 2/2009 | Vullev | ............... G01N 33/5076 435/5 |

(Continued)

FOREIGN PATENT DOCUMENTS

| | | | |
|---|---|---|---|
| WO | WO 2013/050744 A1 | 4/2013 | |
| WO | WO-2021262738 A2 * | 12/2021 | ............. G01N 21/31 |

OTHER PUBLICATIONS

International Search Report and Written Opinion for International Application No. PCT/US2022/035960, mailed Oct. 5, 2022.

(Continued)

*Primary Examiner* — Tarifur R Chowdhury
*Assistant Examiner* — Kemaya Nguyen
(74) *Attorney, Agent, or Firm* — Wolf, Greenfield & Sacks, P.C.

(57) ABSTRACT

Methods for identifying bacterial species in biofluid samples (e.g., whole blood samples) are described. The methods rely on optical spectroscopy, and enable rapid detection and identification of bacteria directly from whole blood. Not only can LSS-based techniques detect and identify bacteria in biofluids such as whole blood, but that species-level identification can potentially be made based on a small number of bacterial cells, without the need for observing entire colonies or performing susceptibility testing. The methods may comprise illuminating the biofluid sample with input light, detecting scattered light produced by the biofluid sample in response to the illuminating, generating first data indicative of a measured scattering spectrum (Continued)

associated with the biofluid sample using the detected scattered light, and identifying whether at least one of the bacterial species is present in the biofluid sample using the first data.

18 Claims, 11 Drawing Sheets

(51) Int. Cl.
  *G01N 33/49*     (2006.01)
  *G01N 21/47*     (2006.01)

(56) References Cited

U.S. PATENT DOCUMENTS

| | | | |
|---|---|---|---|
| 2010/0035235 A1 | 2/2010 | Gabriel | |
| 2020/0297266 A1 | 9/2020 | Perelman | |
| 2021/0033592 A1* | 2/2021 | Ye | G01N 15/1434 |
| 2021/0041341 A1* | 2/2021 | Chen | G01N 33/5094 |

OTHER PUBLICATIONS

International Preliminary Report on Patentability for International Application No. PCT/US2022/035960, mailed Jan. 11, 2024.

Bradley et al., Rapid antibiotic-resistance predictions from genome sequence data for *Staphylococcus aureus* and *Mycobacterium tuberculosis*. Nat Commun. Dec. 21, 2015;6:10063. doi: 10.1038/ncomms10063. 15 pages.

Chance et al., Carbohydrate sulfation effects on growth of Pseudomonas aeruginosa. Microbiology (Reading). Jul. 2000;146 (Pt 7):1717-25. doi: 10.1099/00221287-146-7-1717.

Cheng et al., Rapid (<5 min) Identification Of Pathogen In Human Blood by Electrokinetic Concentration and Surface-Enhanced Raman Spectroscopy. Sci Rep. Aug. 6, 2013;3:2365; 8 pages. doi: 10.1038/srep02365.

Depamphilis et al., Purification of intact flagella from *Escherichia coli* and Bacillus subtilis. Journal of bacteriology. Jan. 1971;105(1):376-83.

Drezek et al., Light scattering from cervical cells throughout neoplastic progression: influence of nuclear morphology, DNA content, and chromatin texture. J Biomed Opt. Jan. 2003;8(1):7-16. doi: 10.1117/1.1528950.

Han et al., Isolation of intact bacteria from blood by selective cell lysis in a microfluidic porous silica monolith. Microsyst Nanoeng. Jun. 17, 2019;5:30. 11 pages. doi: 10.1038/s41378-019-0063-4.

Itzkan et al., Confocal light absorption and scattering spectroscopic microscopy monitors organelles in live cells with no exogenous labels. Proc Natl Acad Sci U S A. Oct. 30, 2007;104(44):17255-60. doi: 10.1073/pnas.0708669104. Epub Oct. 23, 2007.

Kang et al., Rapid detection of single bacteria in unprocessed blood using Integrated Comprehensive Droplet Digital Detection. Nat Commun. Nov. 13, 2014;5:5427. 10 pages. doi: 10.1038/ncomms6427.

Konokhova et al., High-precision characterization of individual *E. coli* cell morphology by scanning flow cytometry. Cytometry A. Jun. 2013;83A:568-75. doi: 10.1002/cyto.a.22294. Epub Apr. 8, 2013.

Layne et al., Transient fluorescence in synchronously dividing *Escherichia coli*. Proc Natl Acad Sci USA. Nov. 1985;82(22):7599-603. doi: 10.1073/pnas.82.22.7599.

Liu et al., Functionalized arrays of Raman-enhancing nanoparticles for capture and culture-free analysis of bacteria in human blood. Nat Commun. Nov. 15, 2011;2:538. 8 pages. doi: 10.1038/ncomms1546.

Männik et al., Robustness and accuracy of cell division in *Escherichia coli* in diverse cell shapes. Proc Natl Acad Sci U S A. May 1, 2012;109(18):6957-62. doi: 10.1073/pnas.1120854109. Epub Apr. 16, 2012.

Melo et al., Cancer exosomes perform cell-independent microRNA biogenesis and promote tumorigenesis. Cancer Cell. Nov. 10, 2014;26(5):707-21. doi: 10.1016/j.ccell.2014.09.005. Epub Oct. 23, 2014.

Mie G., Contributions on the Optics of Turbid Media, Particularly Colloidal Metal Solutions. InBook Annalen Der Physik. Series IV, 1908;25(3):377-445.

Onyango et al., Phenotypic variants of *Staphylococci* and their underlying population distributions following exposure to stress. PLoS One. Oct. 18, 2013;8(10):e77614. 9 pages. doi: 10.1371/journal.pone.0077614.

Schubert et al., Novel, improved sample preparation for rapid, direct identification from positive blood cultures using matrix-assisted laser desorption/ionization time-of-flight (MALDI-TOF) mass spectrometry. J Mol Diagn. Nov. 2011;13(6):701-6. doi: 10.1016/j.jmoldx.2011.07.004. Epub Sep. 1, 2011.

Silhavy et al., The bacterial cell envelope. Cold Spring Harb Perspect Biol. May 2010;2(5):a000414. 17 pages. doi: 10.1101/cshperspect.a000414. Epub Apr. 14, 2010.

Sinha et al., Emerging Technologies for Molecular Diagnosis of Sepsis. Clin Microbiol Rev. Apr. 2018;31(2):e00089-17. 26 pages. doi: 10.1128/CMR.00089-17.

Sokolov et al., Polarized reflectance spectroscopy for pre-cancer detection. Technol Cancer Res Treat. Feb. 2004;3(1):1-14. doi: 10.1177/153303460400300101.

Zheng et al., Optical Scatter Imaging with a digital micromirror device. Opt Express. Oct. 26, 2009;17(22):20401-14. doi: 10.1364/OE.17.020401.

* cited by examiner

| Samples | 360 nm | | 510 nm | | 745 nm | |
|---|---|---|---|---|---|---|
| | A | R | A | R | A | R |
| 1 | 50% | 46.3% | 50% | 53.7% | 0 | 0 |
| 2 | 50% | 48.4% | 0 | 0 | 50% | 51.6% |
| 3 | 0 | 0 | 50% | 45.9% | 50% | 54.1% |
| 4 | 33.3% | 30.4% | 33.3% | 37.4% | 33.3% | 32.2% |

FIG. 2C

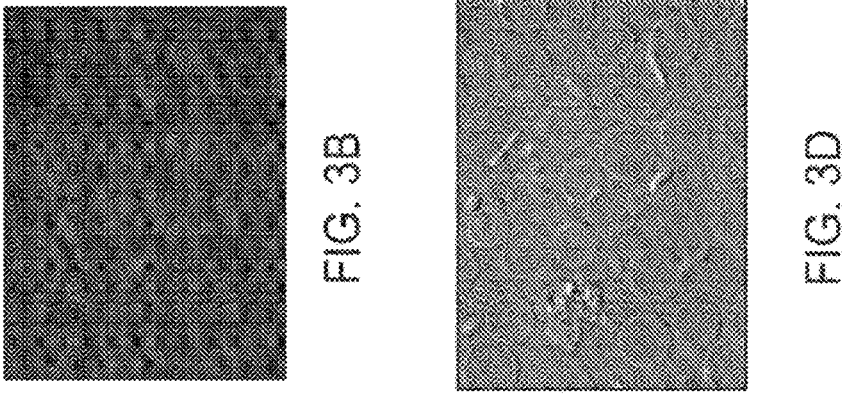
FIG. 3B
FIG. 3D
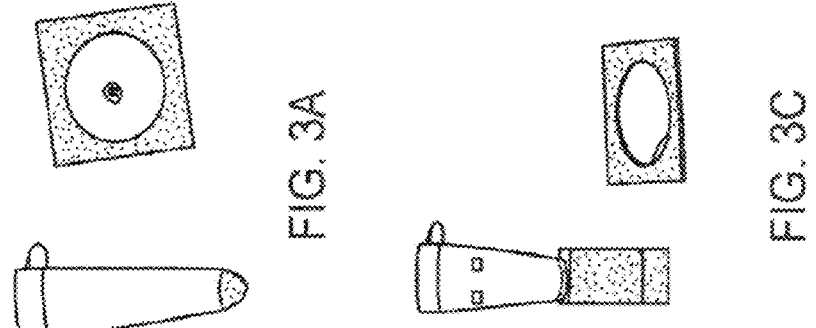
FIG. 3A
FIG. 3C

| Samples | E. coli | | S. aureus | | P. aeruginosa | | K. pneumonia | |
|---|---|---|---|---|---|---|---|---|
| | A | R | A | R | A | R | A | R |
| 1 - 4 | 100% | 95.5% | 0 | 2.8% | 0 | 1.5% | 0 | 0.2% |
| 5 - 8 | 0 | 4.4% | 100% | 90.1% | 0 | 0.1% | 0 | 5.5% |
| 9 - 12 | 0 | 0 | 0 | 0 | 100% | 100% | 0 | 0 |
| 13 - 16 | 0 | 0.2% | 0 | 0 | 0 | 0 | 100% | 99.8% |

FIG. 6C

Begin

701

Lyse the biofluid sample

702
Illuminate the biofluid sample with input light

704
Detect scattered light produced by the biofluid sample

706
Generate first data indicative of a measured scattering spectrum

708
Identify whether at least one bacteria species is present in the biofluid sample 709
Perform Rayleigh correction End

700

RAPID DETECTION AND IDENTIFICATION OF BACTERIA DIRECTLY FROM WHOLE BLOOD WITH LIGHT SCATTERING SPECTROSCOPY BASED BIOSENSOR

CROSS-REFERENCE TO RELATED APPLICATIONS

This Application is a national stage filing under 35 U.S.C. 371 of International Patent Application Serial No. PCT/US2022/035960, filed Jul. 1, 2022, entitled "RAPID DETECTION AND IDENTIFICATION OF BACTERIA DIRECTLY FROM WHOLE BLOOD WITH LIGHT SCATTERING SPECTROSCOPY BASED BIOSENSOR", which claims the benefit under 35 U.S.C. § 119 (e) of U.S. Provisional Patent Application Ser. No. 63/218,184, filed Jul. 2, 2021, entitled "RAPID DETECTION AND IDENTIFICATION OF BACTERIA DIRECTLY FROM WHOLE BLOOD WITH LIGHT SCATTERING SPECTROSCOPY BASED BIOSENSOR," the entire contents of each of which are incorporated herein by reference.

FEDERALLY SPONSORED RESEARCH

This invention was made with Government support under Grant No. CA218382 awarded by the National Institute of Health, and Grant No. CA228029 awarded by the National Institute of Health. The Government has certain rights in the invention.

BACKGROUND

Bacteria are ubiquitous, mostly free-living organisms often consisting of one biological cell. Bacteria inhabit soil, water, acidic hot springs, radioactive waste, and the deep biosphere of Earth's crust. Bacteria display a wide diversity of shapes and sizes. Bacterial cells are about one-tenth the size of eukaryotic cells and are typically 0.5-5.0 micrometres in length. Most bacterial species are shaped as spheres, rods, commas or spirals. The human body is continually exposed to many species of bacteria, including beneficial commensals. If bacteria form a parasitic association with other organisms, they are classed as pathogens. Pathogenic bacteria are a major cause of human death and disease and cause infections such as tetanus and tuberculosis.

SUMMARY

Some embodiments relate to a method for identifying bacterial species in a biofluid sample, comprising: illuminating the biofluid sample with input light; detecting scattered light produced by the biofluid sample in response to the illuminating; generating first data indicative of a measured scattering spectrum associated with the biofluid sample using the detected scattered light; and identifying whether at least one of the bacterial species is present in the biofluid sample using the first data.

In some embodiments, identifying whether at least one of the bacterial species is present in the biofluid sample comprises: obtaining second data indicative of a plurality of reference scattering spectra, each reference scattering spectrum being associated with a respective one of the bacterial species; generating third data indicative of a linear combination of the reference scattering spectra, the linear combination comprising a plurality of unknown coefficients representing respective concentrations for the bacterial species in the biofluid sample; and determining the unknown coefficients using the first data and the third data.

In some embodiments, determining the unknown coefficients comprises generating an equation based on a comparison of the first data with the third data.

In some embodiments, determining the unknown coefficients comprises applying a linear minimization approach to the equation.

In some embodiments, identifying whether at least one of the bacterial species is present in the biofluid sample comprises performing Rayleigh correction of the first data.

In some embodiments, the method further comprises integrating the first data, wherein identifying whether at least one of the bacterial species is present in the biofluid sample comprises identifying whether at least one of the bacterial species is present in the biofluid sample using the integrated first data.

In some embodiments, illuminating the biofluid sample with the input light comprises illuminating a blood sample with the input light; and detecting the scattered light scattered by the biofluid sample in response to the illuminating comprises detecting the scattered light produced by the blood sample in response to the illuminating.

In some embodiments, illuminating the biofluid sample with the input light comprises illuminating the biofluid sample with polarized input light.

In some embodiments, the polarized input light is polarized in a direction substantially perpendicular to a scattering plane associated with the scattered light.

In some embodiments, detecting the scattered light produced by the biofluid sample comprises polarizing the scattered light and detecting the polarized scattered light.

In some embodiments, polarizing the scattered light comprises polarizing the scattered light in a direction substantially perpendicular to a scattering plane associated with the scattered light.

In some embodiments, identifying whether at least one of the bacterial species is present in the biofluid sample comprises identifying whether at least one of a *Pseudomonas aeruginosa*, an *Escherichia coli*, a *Klebsiella pneumoniae*, a *Staphylococcus aureus*, a *Streptococcus pneumoniae*, a *Listeria monocytogenes*, a *Staphylococcus epidermidis*, a *Staphylococcus haemolyticus*, a *Neisseria meningitidis*, a *Haemophilus influenzae*, and a *Proteus mirabilis* is present in the biofluid sample.

In some embodiments, the method further comprises, prior to illuminating the biofluid sample with the input light, lysing red blood cells from the biofluid sample.

In some embodiments, lysing the red blood cells from the biofluid sample comprises mixing the biofluid sample with water.

In some embodiments, identifying whether at least one bacterial species is present in the biofluid sample comprises determining a relative concentration of the at least one bacterial species with respect to other bacterial species.

Some embodiments relate to a system for identifying bacterial species in a biofluid sample, comprising: a light source; a spectrograph and a photosensitive detector; first and second polarizers, the first polarizer being disposed on a first optical path formed between the light source and the biofluid sample and the second polarizer being disposed on a second optical path formed between the biofluid sample and the spectrograph; and a processor coupled to the photosensitive detector and configured to: generate first data indicative of a measured scattering spectrum associated with the biofluid sample; and identify whether at least one of the bacterial species is present in the biofluid sample using the first data.

In some embodiments, the processor is configured to identify whether at least one of the bacterial species is present in the biofluid sample by: obtaining second data indicative of a plurality of reference scattering spectra, each reference scattering spectrum being associated with a respective one of the bacterial species; generating third data indicative of a linear combination of the reference scattering spectra, the linear combination comprising a plurality of unknown coefficients representing respective concentrations for the bacterial species in the biofluid sample; and determining the unknown coefficients using the first data and the third data.

In some embodiments, the processor is configured to determine the unknown coefficients by generating an equation based on a comparison of the first data with the third data.

In some embodiments, the processor is configured to identify whether at least one of the bacterial species is present in the biofluid sample by performing Rayleigh correction of the first data.

In some embodiments, the first polarizer has a polarization axis substantially perpendicular to a scattering plane associated with scattered light produced by the biofluid sample in response to illumination by the light source, and the second polarizer has a polarization axis substantially perpendicular to the scattering plane.

In some embodiments, the light source comprises a xenon-arc lamp.

BRIEF DESCRIPTION OF DRAWINGS

Various aspects and embodiments will be described with reference to the following figures. It should be appreciated that the figures are not necessarily drawn to scale. In the drawings, each identical or nearly identical component that is illustrated in various figures is represented by a like numeral. For purposes of clarity, not every component may be labeled in every drawing.

FIG. 2C is a table illustrating the relative particle concentrations of the samples of FIG. 2B, in accordance with some embodiments of the technology described herein.

FIG. 3A illustrates a sample of *E. coli* bacteria in whole blood, in accordance with some embodiments of the technology described herein.

FIG. 3B illustrates a DIC microscopy image of the sample of FIG. 3A, in accordance with some embodiments of the technology described herein.

FIG. 3C illustrates a sample of *E. coli* bacteria in whole blood after lysing, in accordance with some embodiments of the technology described herein.

FIG. 3D illustrates a DIC microscopy image of the sample of FIG. 3C, in accordance with some embodiments of the technology described herein.

FIG. 6C is a table illustrating the relative particle concentrations of sixteen samples, in accordance with some embodiments of the technology described herein.

DETAILED DESCRIPTION

I. Overview

Figure 1A:
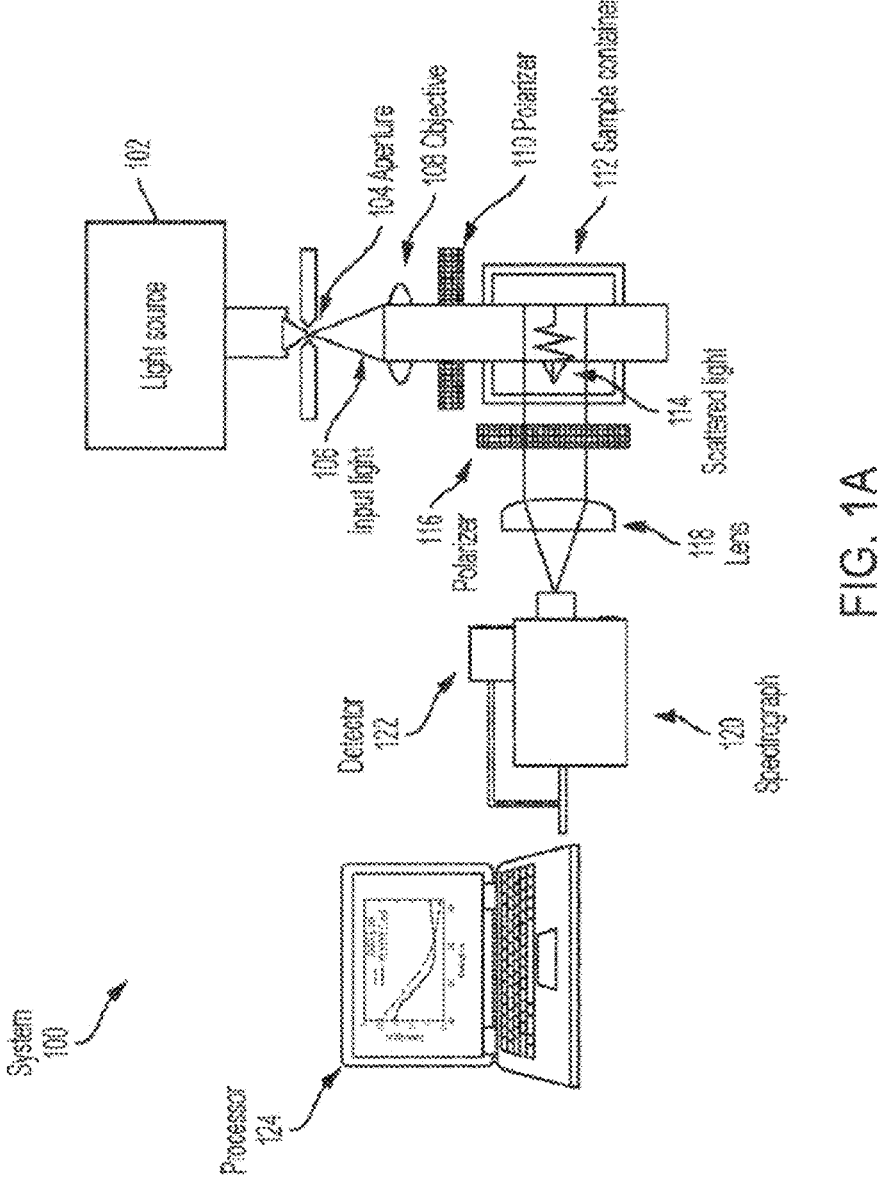
FIG. 1A is a block diagram of a system for identifying bacterial species, in accordance with some embodiments of the technology described herein.

Bacterial infections, which can cause sepsis and septic shock, are one of the major causes of death worldwide. More than three million antibiotic-resistant bacterial infections occur in the U.S. each year and more than 50,000 people die as a result. Sepsis occurs in 1-2% of all hospitalizations in the U.S., but accounts for 17% of in-hospital deaths. Presently, the identification of a bacterial species that is the source of an infection takes anywhere from several days to a week. This long identification time exceeds the treatment window for seriously ill patients and a broad-spectrum antibiotic treatment is initiated based on other information from the patient assessment. However, the choice of antimicrobial agent is a guess, which is often incorrect, resulting in the death of the patient in approximately 40% of severe sepsis cases, with every hour delay in the correct antimicrobial prescription reducing the survival rate by 7.6%. Many of these deaths are preventable if the bacterial species can be identified quickly, allowing a more specific antibiotic treatment to be initiated immediately. Additionally, the fast identification of bacterial species in non-emergency scenarios will reduce the likelihood of emerging bacterial strains with antibiotic resistance, and improve patient response to treatment. Given the high financial costs associated with treating new antimicrobial-resistant strains of bacteria, reducing their likelihood can significantly reduce healthcare costs.

Current clinical methods for bacterial identification depend on culture (e.g., blood culture, urine culture, sputum culture). To perform a culture, a sample of body fluid is added to bacterial broth media. This sample is maintained at body temperature and monitored over a period of up to 5 days. Bacteria that are easy to culture can be identified within one or two days, while bacteria that are more difficult to culture may take up to five days to culture, or may not give a positive result at all. After a bacteria is cultured, it is plated and tested for antibiotic susceptibility in order to identify the species. This is another time-consuming step. Other methods have shown bacterial identification through polymerase chain reaction (PCR), even at earlier stages in the process. However, a bacteria-specific primer is required for PCR to be successfully used and primers are typically not available for a large number of bacterial species.

Several attempts have been made to decrease the time it takes to identify the bacterial species in blood or other biofluid samples by performing bacteria detection without culture directly from whole blood. The techniques employ various flavors of nucleic acid amplification, such as Iridica Plex ID, SeptiFast, MinION nanopore sequencing or amplification-free technologies, such as a droplet digital detection technology IC 3D. However, the majority of these techniques still suffer from common problems of inability to detect non-targeted pathogens and a long (at least several hours) turnaround time, which so far, has limited their ability to make a large impact on patient treatment decisions.

Recognizing the inadequacy of conventional techniques, Applicant has developed a novel approach for rapid detection and identification of bacteria directly from whole blood using light scattering spectroscopy (LSS) based techniques. As discussed herein, not only can LSS-based techniques detect and identify bacteria in biological fluids (biofluids) such as whole blood, but that species-level identification can potentially be made based on a small number of bacterial cells, without the need for observing entire colonies or performing susceptibility testing. These methods detect physical and biochemical properties of bacteria related to their sizes, shapes and refractive indices, utilizing principles of LSS. The inexpensive LSS bacteria detection and identification techniques do not require complex sample preparation. For example, in some embodiments, preprocessing involves adding distilled cold water to a whole blood sample to lyse the red blood cells, steering it and waiting for approximately a few minutes (e.g., three) for the cell debris to settle. Cold water induces blood cells swelling followed by cell rupture due to hypotonic shock, while bacteria are kept intact because they have a rigid exoskeleton composed of peptidoglycan, which protects them from osmotic pressure.

In LSS-based detection, unlike in PCR, free DNA from lysed cells does not interfere with the measurement because the signal is dominated by the largest scatterer in the suspension. Furthermore, species-level identification can be made based on a small number of bacterial cells without the need for susceptibility testing involving bacterial colonies' growth. Sample preparation with LSS system takes only a few minutes, while spectroscopic measurements are performed in several seconds, which makes the methods described herein ideal for rapid detection and identification of bacteria directly from whole blood in hospital or ambulatory settings, or even in the field.

In some embodiments, the methods described herein differentiate bacteria based on their size, shape and/or refractive index. As a result, individual strains of the same bacterial species have remarkably reproducible shapes and narrow distributions of sizes. For example, the strain of *S. aureus* bacteria discussed herein is the methicillin-sensitive (MSSA) strain, which accounts for 95.7% of all *S. aureus* caused sepsis. This bacteria have a spherical shape and are approximately 100 nm smaller than the other strain of *S. aureus* which is methicillin-resistant (MRSA). This difference in size is significantly larger than the accuracy of the LSS measurements. Moreover, according to the standard of care, each of the bacterial species is treated with just several very specific antibiotics. For example, independently of the strain, *S. aureus* is treated with penicillin. Thus, the identification of bacterial species with the LSS system would immediately result in a very significant reduction in the choice of antibiotics used for treatment.

In some embodiments, the methods discussed herein may be optimized for identifying bacteria from blood for rapid sepsis diagnostics. In some embodiments, these methods are capable of achieving bacteria detection in concentrations as low as $10^3$ CFU/mL in blood, in approximately three minutes, giving the physician immediate information. Therefore, due to the simplicity and feasibility for manipulation, these methods could potentially be adapted as part of a rapid clinical laboratory routine.

II. Systems for Light Scattering Spectroscopy

LSS involves detection of a light scattering spectrum that depends on the fundamental characteristics of the particles, such as their size and refractive index. LSS typically utilizes the convenient approximation of assuming that the particles can be adequately modeled as spheres of unknown size and refractive index. The exact solution of light scattering by spheres can be solved using Mie theory—the results depend on the diameter of the sphere, the relative refractive index, the wavelength of light, the polarization, observation angle, and distance to the particle.

FIG. 1A is a block diagram of a system for identifying bacterial species, in accordance with some embodiments of the technology described herein. System 100 includes a light source 102, an aperture 104, an objective 108, a polarizer 110, a sample container 112, a polarizer 116, a lens 118, a spectrograph 120, a photosensitive detector 122 and a processor 124. Light source 102 may include a source of white light, an example of which is a xenon-arc lamp. In some embodiments, light source 102 may output high optical power, for example as high as 75 W. Input light 106 identifies the light produced by light source 102, which in some embodiments may be passed through aperture 104. Objective 108 focuses the input light on the sample, and optionally may provide optical magnification (e.g., 10× magnification). Polarizer 110 polarizes input light 106 and polarizer 116 polarizer polarizes scattered light 114. Thus, polarizer 110 is disposed on a first optical path formed between the light source 102 and the biofluid sample and polarizer 116 is disposed on a second optical path formed between the biofluid sample and the spectrograph 120. In some embodiments, both polarizers polarize in a direction perpendicular to the scattering plane of the sample (e.g., the plane that includes the source, the scattering particle and the observer). Applicant has appreciated that by polarizing the input light and detecting the component of the scattered light perpendicularly polarized relative to the scattering plane, the contribution of multiple scattering can be reduced, thus increasing the bacteria-specific contribution of a single scattering.

Sample container 112 contains a biofluid sample. Sample container may be transparent, and may be shaped in any suitable way. For example, it may be arranged as a glass cuvette (e.g., square-shaped) with any suitable path length (e.g., 1 cm). The sample contained in the sample container 112 may include a liquid suspension of individual strains of bacteria, mixtures of various strains of bacteria, or samples of bacteria in human blood, among other examples.

Lens 118 focuses scattered light 114—the light scattered by the biofluid sample in response to illumination by input light 106—on the input slit of spectrograph 120. For example, lens 118 may be a cylindrical lens. Spectrograph 120 separates the scattered light in accordance with its spectral components, and conveys the spectral components to photosensitive detector 122. As a result, the system can detect optical spectra. Detector 122 may provide light detection in the 450-700 nm wavelength range, for example. In some embodiments detector 122 may be implemented using a charge-coupled device (CCD). Processor 124 (which may be part of a computer as shown in FIG. 1A or any other suitable type of digital electronic system) may process data generated using the detector, as discussed in detail further below. Processor 124 may be coupled to detector 122 and spectrograph 120.

Figure 1B:
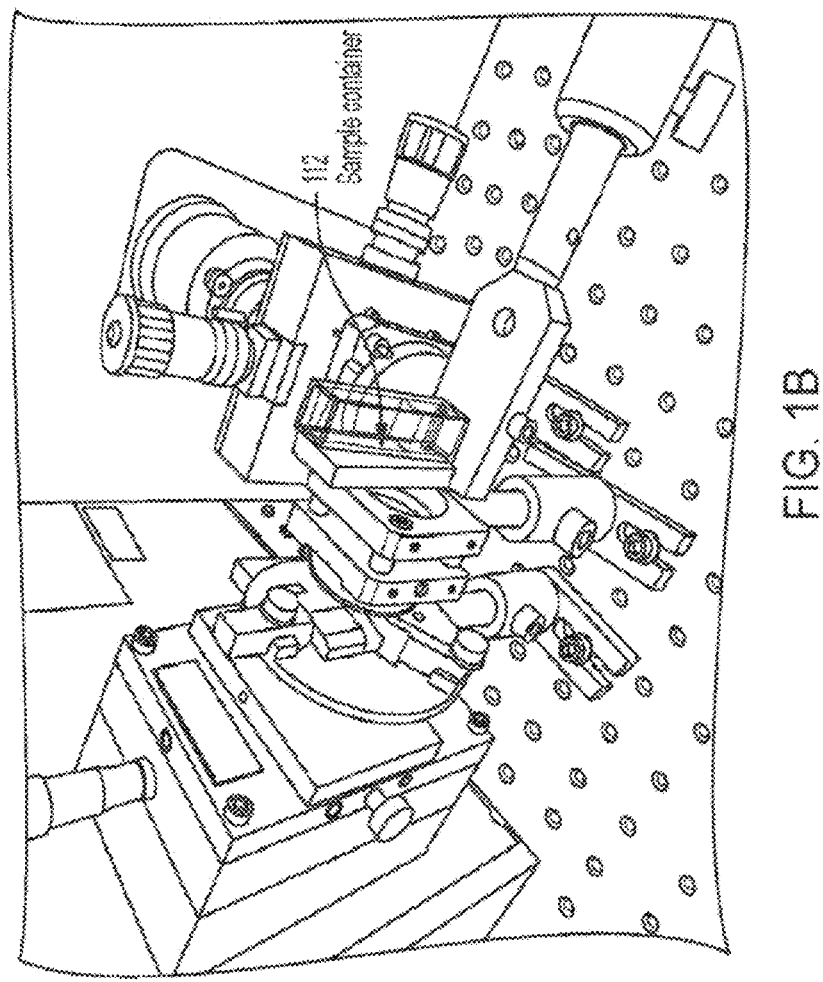
FIG. 1B is a photograph of an example setup implementing the system of FIG. 1A, in accordance with some embodiments of the technology described herein.

FIG. 1B is a photograph of an example setup implementing the system of FIG. 1A, in accordance with some embodiments of the technology described herein. In this example, system 100 is implemented on an optical bench, and sample container 112 as a 1 cm-path length, square-shape glass cuvette.

III. Calibration

In order to calibrate the LSS system and establish the ability of LSS to detect and differentiate submicrometer particles, experiments were performed with polystyrene microspheres with four different diameters: 82±6 nm, 380±15 nm, 510±11 nm, and 745±10 nm suspended in water, with diameters and standard deviations provided by the manufacturer (Polyscience, Inc). 82 nm microspheres were used to calculate the ratio of the Mie theory-based spectrum for the 90-degree scattering and the experimental spectrum. By multiplying that ratio on the spectra of the 380 nm, 510 nm, and 745 nm microspheres, calibrated spectra were obtained with the characteristics of the experimental system taken into account.

Figure 2B:
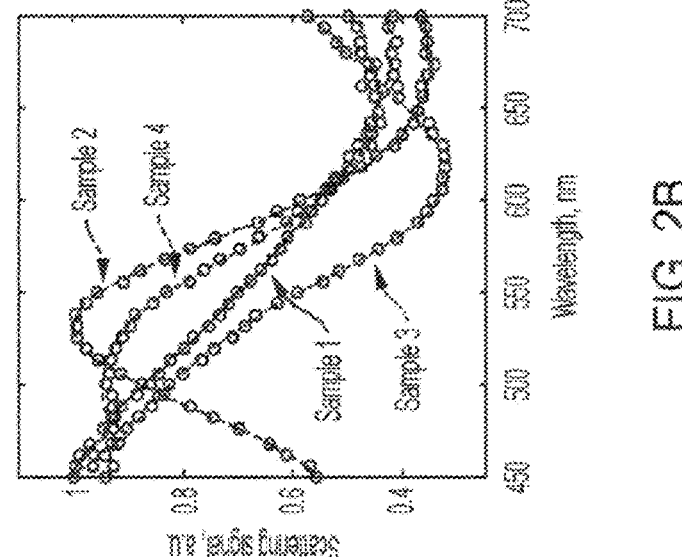
FIG. 2B is a plot illustrating scattering spectra associated with different samples, in accordance with some embodiments of the technology described herein.
Figure 2A:
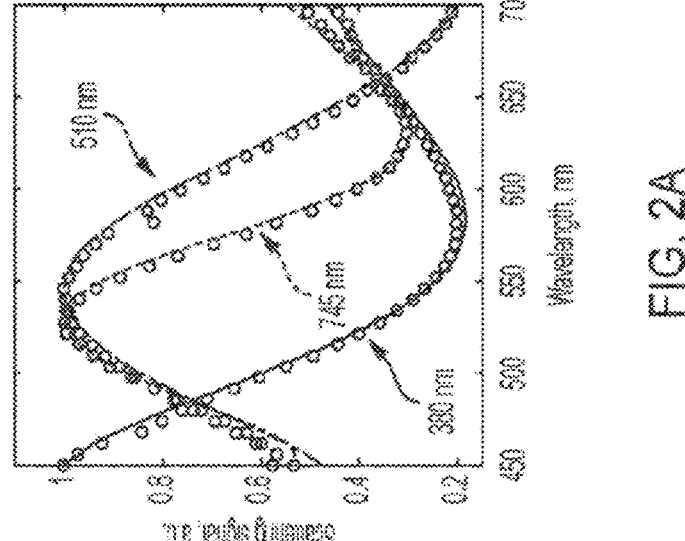
FIG. 2A is a plot illustrating scattering spectra associated with particles of different sizes, in accordance with some embodiments of the technology described herein.

FIG. 2A is a plot illustrating scattering spectra associated with particles of different sizes—namely, 380 nm, 510 nm and 745 nm. The spectra obtained using Mie theory were fitted to the calibrated experimental data using linear minimization (e.g., least-squares minimization). In FIG. 2A, the circles represent the LLS experimental data and the solid lines represent the spectra obtained using Mie theory. The reconstructed mean sizes and standard deviations of the microspheres were 390±14 nm, 500±10 nm, and 735±8 nm, in reasonable agreement with the manufacturer provided specifications for all sizes of microspheres used in the experiments. Based on these experiments, the accuracy of the LSS experimental system and algorithm is estimated to be about 10 nm.

IV. Methods for Identifying Concentrations

Methods for identifying individual scatterers present in the interrogation volume of the LSS system were further developed. The approach does not require Mie theory based modeling of the scatterers' spectra, but can just employ a prior compiled LSS library of spectra of individual scatterers, such as various types of bacteria strains, to obtain their concentrations. In this case, no assumptions about the bacteria shapes or refractive indices may be needed. The experimentally measured LSS spectrum can be presented as a weighted sum of the spectra of the scatterers present in the interrogation volume, in accordance with the following equation:

$$S(\lambda) = \sum_{i=1}^{N} c_i S_i(\lambda) + \varepsilon(\lambda)$$

where N represents the number of scatterers, $S_i(\lambda)$ represent the spectra of individual components present in the LSS library, the $c_i$ coefficients represent the respective concentrations, and $\varepsilon(\lambda)$ represents the error which includes the experimental noise of the system, as well as the contributions of unknown scatterers that may exist in the sample. In that case, the concentrations of the components could be found by employing the linear minimization approaches (e.g., the least square minimization approach, as shown below):

$$\sum_{\lambda} \left( S(\lambda) - \sum_{i=1}^{N} c_i S_i(\lambda) \right)^2 \Rightarrow \min$$

To test the performance of this approach, three binary and one ternary mixtures of polystyrene microspheres were measured in water. The reconstructed spectra of the mixtures are presented in FIG. 2B, and the related concentrations are shown in the table of FIG. 2C. In FIG. 2B, "sample 1" represents a binary mixture of 380 nm-particles and 510 nm-particles, "sample 2" represents a binary mixture of 510 nm-particles and 745 nm-particles, "sample 3" represents a binary mixture of 380 nm-particles and 745 nm-particles, and "sample 4" represents a ternary mixture of 380 nm-particles, 510 nm-particles, and 745 nm-particles. The table of FIG. 2C illustrates reconstructed concentrations from mixtures of 380 nm, 510 nm, and 745 nm microspheres using LSS spectra. For each of the samples of FIG. 2B, the columns "A" provide actual relative concentrations of the microspheres and the columns "R" provide the reconstructed concentrations. As can be appreciated from the table, this approach can reconstruct the relative concentrations of the scatterers in the mixtures with a better than 95% accuracy.

V. Preparation of Bacteria Samples in Water and Whole Blood

Four typical gram-positive and gram-negative bacteria strains, *Pseudomonas* (P.) *aeruginosa*, *Escherichia* (E.) *coli*, *Klebsiella* (K.) *pneumoniae* and *Staphylococcus* (S.) *aureus*, were purchased from American Type Culture Collection (ATCC) and were cultured according to the ATCC guidelines. Two strains, *P. aeruginosa* and *S. aureus*, were streaked onto trypticase soy agar plates, *E. coli* was streaked onto Luria-Bertani (LB) agar plates and *K. pneumoniae* was streaked onto Difco™ Nutrient plates. After overnight incubation at 37° C., a single colony of each strain was cultivated in 10 mL of the respective broth at 37° C. with shaking at 200 rpm. *P. aeruginosa* and *S. aureus* were grown in trypticase soy broth; *E. coli* in LB broth and *K. pneumoniae* in Difco™ Nutrient broth. After 14 to 16 hours of incubation, suspension of each bacteria was centrifuged at 2000 g for 10 minutes at room temperature. The pellets of bacteria were resuspended with 10 mL of phosphate-buffered saline (PBS) and centrifuged (2000 g, 10 min, room temperature). This washing procedure was repeated twice to remove any culture broth residue. After the final wash, bacteria were suspended in PBS.

The optical density (OD) of suspensions was then measured with a BIO-RAD SmartSpec Plus spectrophotometer at 600 nm and correlated with bacteria number densities in suspensions. The same amount (10 mL) of each culture medium without inoculating bacteria was incubated for 14 to 16 hours, centrifuged, washed twice and resuspended with PBS, serving as blanks for OD measurements or negative controls for LSS measurements. The concentration of resuspended bacteria was determined using spectrophotometry. This cell concentration was reconfirmed by spiral plating the suspension onto the respective agar pates to obtain total viable counts.

To perform LSS measurements, each bacteria sample was resuspended in Milli-Q water to obtain $10^7$ CFU/mL, $10^5$ CFU/mL, $10^4$ CFU/mL and $10^3$ CFU/mL concentrations, which were confirmed by spectrophotometry. The LSS spectra for each 400 µL bacteria sample placed in a 1 cm path length square glass cuvette were collected at room temperature using an integration time of 10 s (0.1 s with 100 repeats). For each concentration, three samples were prepared, and three measurements were performed on each sample.

Bacterial samples in whole blood were prepared by mixing 50 µL of bacteria suspensions in PBS at concentrations of $10^7$ CFU/mL with whole blood obtained from healthy adult volunteers. The resulting concentration of bacteria in whole blood was $10^3$ CFU/mL. The protocol was reviewed by the BIDMC Institutional Review Board, and the requisite approvals were obtained.

FIG. 3A illustrates a sample of *E. coli* bacteria in whole blood, obtained for realistic bacterial concentration in blood during mild sepsis, and FIG. 3B illustrates a DIC micros-copy image of the sample. To minimize contribution of red blood cells in the samples, the cells were lysed by hypotonic shock using cold water. Bacteria samples in whole blood (200 µL) were mixed with ice-cold Milli-Q water (600 µL). When red blood cells lyse, the hemoglobin spreads through-out the sample, making it look pinkish. However, the medium inside and outside of the cell becomes the same, making the scattering cross section of the cell ghost to be approximately 0.1% of the cross section of the intact red blood cell. As scattering is significantly reduced, the solution becomes significantly more clear. The mixtures were lightly agitated for 2 min or until the solution became fully clear which indicated that red blood cells lysis was complete. FIG. 3C illustrates the same sample shown in FIG. 3A but after adding Milli-Q water to lyse the cells, and FIG. 3D illus-trates a DIC microscopy image of the lysed sample. Prior to the LSS measurements, the samples were kept still for 3 min at room temperature, allowing the cell debris to settle.

It should be noted that although there are a number of commercially available lysing products or reagents that can lyse red blood cells more efficiently, hypotonic shock using ice-cold water was ultimately selected. This choice was made because chemical disruption of the red blood cell membrane with detergents or alkali materials employed in chemical lysis can alter the properties of the bacterial sample. In addition, some red blood cell lysis buffers are specially formulated to be used for DNA or RNA isolation from blood, which is not suitable for the detection of bacteria.

It should also be noted that 80% of all sepsis infections in hospitals are due to the four bacteria species described above. By adding seven additional bacteria species (*Strep-tococcus pneumoniae*, *Listeria monocytogenes*, *Staphylo-coccus epidermidis*, *Staphylococcus haemolyticus*, *Neis-seria meningitidis*, *Haemophilus influenzae*, and *Proteus mirabilis*), this number can be brought to approximately 95%. Therefore, by increasing the LSS bacteria library to include these eleven bacteria species, one should be able to rapidly identify the sepsis causing bacteria in the majority of clinical cases.

VI. Detection and Identification of Bacteria in Water Suspensions

Figure 4A:
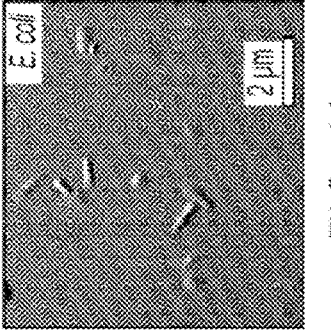
FIG. 4A is a microphotograph of a sample including *E. coli*, in accordance with some embodiments of the technology described herein.
Figure 4B:
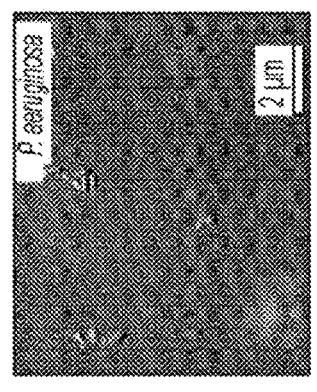
FIG. 4B is a microphotograph of a sample including *P. aeruginosa*, in accordance with some embodiments of the technology described herein.
Figure 4C:
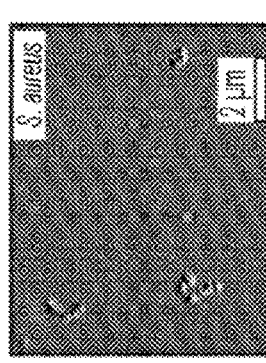
FIG. 4C is a microphotograph of a sample including *S. aereus*, in accordance with some embodiments of the technology described herein.
Figure 4D:
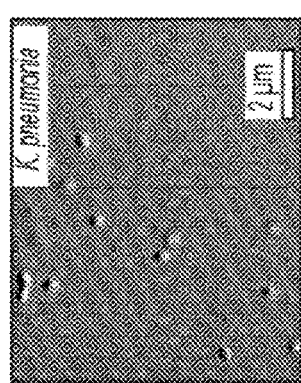
FIG. 4D is a microphotograph of a sample including *K. pneumonia*, in accordance with some embodiments of the technology described herein.
Figure 4E:
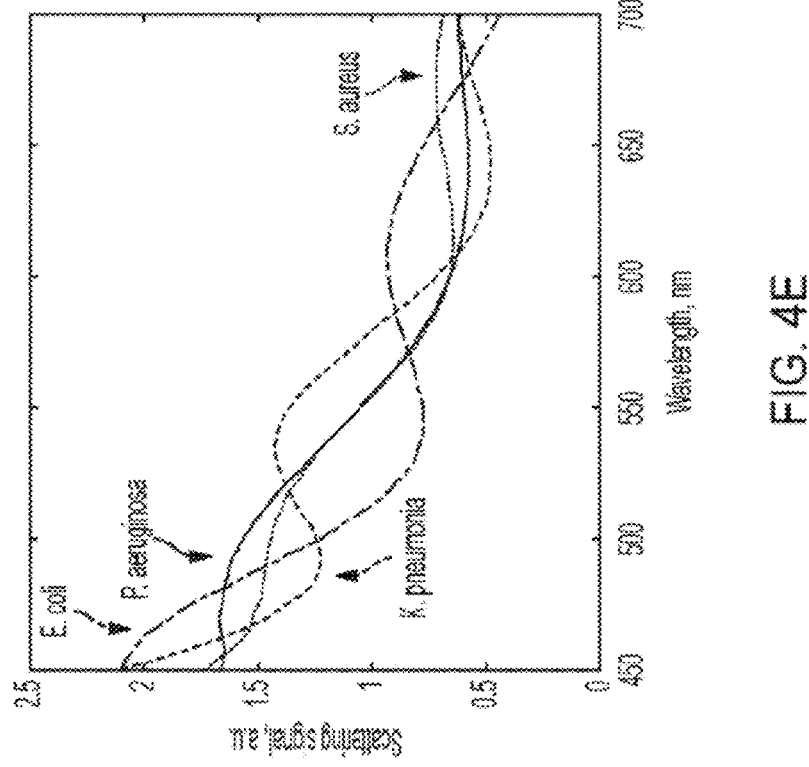
FIG. 4E is a plot illustrating spectra associated with the bacteria of FIGS. 4A-4D, in accordance with some embodiments of the technology described herein.

LSS experiments were performed with water suspensions of four bacterial species: *E. coli*, *K. pneumonia*, *P. aerugi-nosa*, and *S. aureus*. These four species account for nearly 80% of the total sepsis cases caused by specific bacteria. To establish that each bacteria strain has a unique, easily identifiable LSS spectrum, initial measurements were per-formed at the relatively high concentration of $10^7$ CFU/mL. FIG. 4A is a microphotograph of a sample including *E. coli*; FIG. 4B is a microphotograph of a sample including *P. aeruginosa*; FIG. 4C is a microphotograph of a sample including *S. aereus*; and FIG. 4D is a microphotograph of a sample including *K. pneumonia*. The microphotographs of the bacteria depicted in FIGS. 4A-4D show that it is not practical to differentiate *E. coli* from *P. aeruginosa*, or *S. aureus* from *K. pneumonia* just using their microscopic appearance. However, LSS spectra of the bacteria strains are rather unique, as can be appreciated from FIG. 4E, clearly differentiating each type of bacteria. The LSS spectra of bacteria presented in FIG. 4B are linear combinations of three components: (1) LSS spectra of bacteria in the sample $S_b(\lambda)$ averaged over all possible orientations of the bacteria, (2) LSS spectra of small (under 100 nm) particles always present in the suspension, which has a typical $1/\lambda^4$ Rayleigh wavelength behavior, and (3) experimental noise. Applicant has appreciated that the Rayleigh contribution should be removed from the spectrum to obtain meaningful spectra free of undesired components. The process of removing Rayleigh contribution from a spectrum is referred to as Rayleigh correction.

Figure 5A:
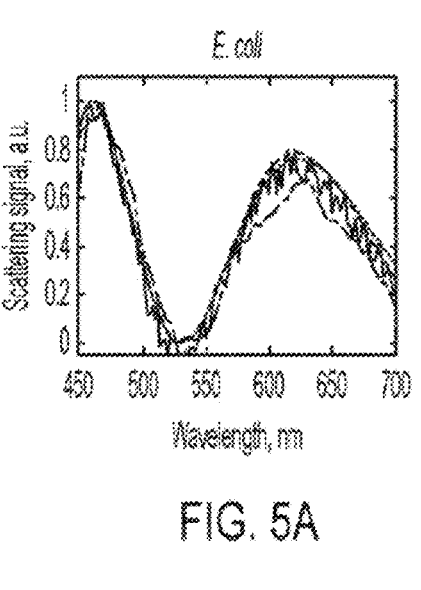
FIG. 5A is a plot illustrating LSS spectra associated with strains of *E. coli*, in accordance with some embodiments of the technology described herein.
Figure 5B:
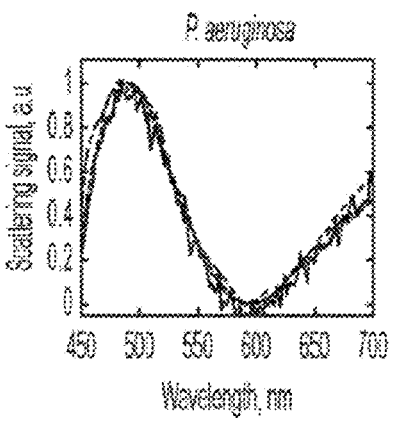
FIG. 5B is a plot illustrating LSS spectra associated with strains of *P. aeruginosa*, in accordance with some embodiments of the technology described herein.
Figure 5C:
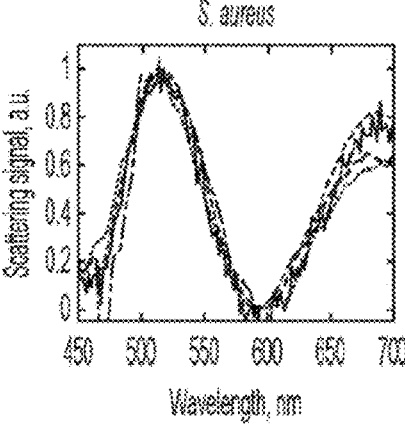
FIG. 5C is a plot illustrating LSS spectra associated with strains of *S. aureus*, in accordance with some embodiments of the technology described herein.
Figure 5D:
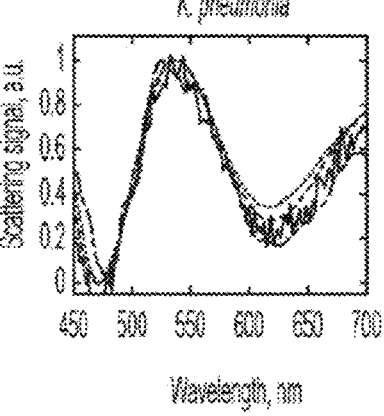
FIG. 5D is a plot illustrating LSS spectra associated with strains of *K. pneumonia*, in accordance with some embodiments of the technology described herein.

The LSS spectra obtained upon performing Rayleigh correction for concentrations of bacterial strains of $10^7$, $10^5$, $10^4$ and $10^3$ CFU/mL are presented in FIG. 5A (*E. coli*), FIG. 5B (*P. aeruginosa*), FIG. 5C (*S. aureus*) and FIG. 5D (*K. pneumonia*). These figures clearly demonstrate that each bacteria type has a unique and reproducible $S_b(\lambda)$. More-over, even at concentrations of $10^3$ CFU/mL, which is the characteristic of mild sepsis, the bacteria spectra are still easily recognizable despite the presence of a certain amount of noise in the spectra. These experimental Rayleigh cor-rected-LSS spectra can serve as markers for bacteria iden-tification. No assumption about the bacteria shapes or refrac-tive indices may be required. FIGS. 5A-5D further illustrate that the spectral shapes are independent from the concen-tration of bacteria.

VII. Rapid Detection and Identification of Bacteria in Whole Blood

Figure 6B:
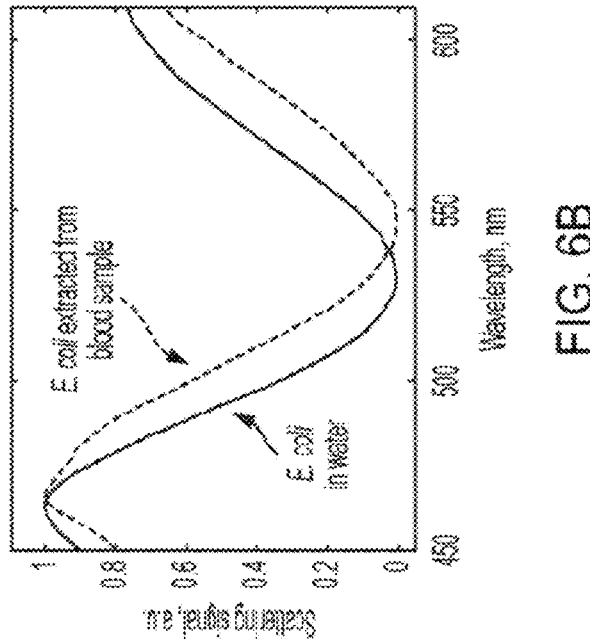
FIG. 6B illustrates LSS spectrum obtained for *E. coli* bacteria extracted from a whole blood sample and from water upon performing Rayleigh correction, in accordance with some embodiments of the technology described herein.
Figure 6A:
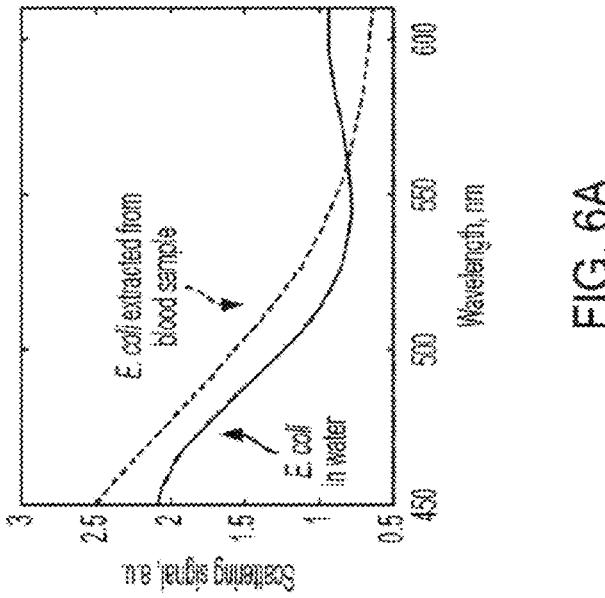
FIG. 6A illustrates raw LSS spectrum obtained for *E. coli* bacteria extracted from a whole blood sample and from water, in accordance with some embodiments of the technology described herein.

Measurements were performed in whole blood samples to test the feasibility of the LSS technique in detecting and identifying bacteria relevant to sepsis treatment clinical conditions. Sixteen samples were prepared, with samples 1 through 4 having *E. coli* in whole blood, samples 5 through 8 having *S. aureus*, samples 9 through 12 having *P. aeruginosa*, and samples 13 through 16 having *K. pneumonia*. Red blood cells are present in a whole blood sample and are significantly larger than bacteria. Given that red blood cells have a different scattering spectrum, the overall amount of light scattering from red blood cells could mask the response of the bacteria. This issue was addressed by lysing red blood cells by hypotonic shock using cold water. After the cell lysis, the samples were kept still for 3 min at room temperature, allowing the cell debris to settle. FIG. 6A illustrates raw LSS spectrum obtained for *E. coli* bacteria extracted from a whole blood sample. The LSS spectrum obtained for *E. coli* bacteria extracted from water is also illustrated, for reference. FIG. 6B illustrates LSS spectrum obtained for *E. coli* bacteria extracted from a whole blood sample upon performing Rayleigh correction. Again, the LSS spectrum obtained for *E. coli* bacteria extracted from water is also illustrated in FIG. 6B, for reference.

Since the majority of clinical sepsis cases contain dangerous amounts of just one bacteria type within the patient's blood, and given that this bacteria should be rapidly identified, only one type of bacteria was present in each of the testing samples. Using the spectral unmixing approach described herein, relative concentrations of bacteria were reconstructed in each of the samples. The results are shown in the table of FIG. 6C, where the first column for each bacteria strain shows the actual percentages of bacteria in four samples, and the second column provides the average percentages reconstructed from the LSS measurements. For example, for samples 1 through 4, an average percentage of *E. coli* to be more than 95% was obtained, with three outliers giving less than 5% in total. The overall accuracy of the LSS method in identification of bacteria in blood samples appears to be approximately 97%.

Although the integration time for LSS measurements was ten seconds, the overall procedure time was approximately three minutes when two preparation steps of red blood cell lysis and cell debris settlement are taken into account. Accordingly, the LSS method is capable of rapid detection and identification of bacteria strains in whole blood samples at bacteria concentrations characteristic of the mild sepsis.

VIII. Methods for Identifying Bacterial Species in Biofluid Samples

Figure 7:
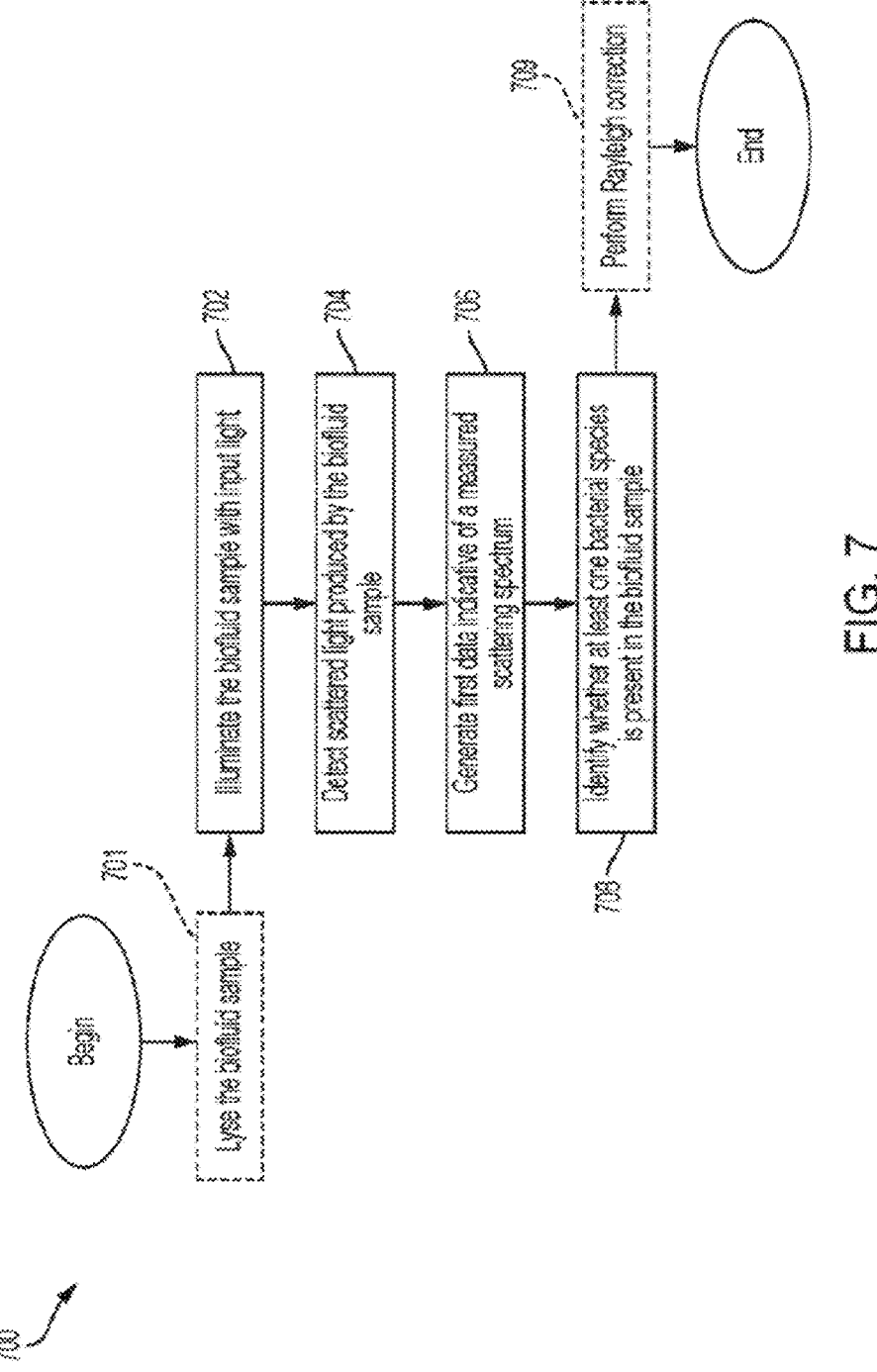
FIG. 7 is a flowchart illustrating a method for identifying bacterial species in a biofluid sample, in accordance with some embodiments of the technology described herein.

FIG. 7 is a flowchart illustrating a method for identifying bacterial species in a biofluid sample, in accordance with some embodiments of the technology described herein. Examples of bacterial species that may be identifying using method 700 include, but are not limited to, *Pseudomonas aeruginosa*, *Escherichia coli*, *Klebsiella pneumoniae*, *Staphylococcus aureus*, *Streptococcus pneumoniae*, *Listeria monocytogenes*, *Staphylococcus epidermidis*, *Staphylococcus haemolyticus*, *Neisseria meningitidis*, *Haemophilus influenzae*, and *Proteus mirabilis*.

Optionally, the biofluid sample to be analyzed in the subsequent steps may be lysed at step 701. In some embodiments, lysing may comprise mixing the biofluid with water (e.g., distilled water).

At step 702, in which a biofluid sample (e.g., a whole blood sample) is illuminated with input light. As an example, referring to FIG. 1A, light source 102 may illuminate a sample disposed in sample container 112 at step 702. In some embodiments, the input light is polarized prior to illuminating the sample, for example using polarizer 110 of FIG. 1A. Accordingly, step 702 may comprise illuminating the biofluid sample with polarized input light. The polarized input light may be polarized in a direction substantially perpendicular to the scattering plane associated with the scattered light.

At step 704, scattered light produced by the biofluid sample in response to the illumination of step 702 is detected. In some embodiments, the scattered light is polarized, for example using polarizer 116 of FIG. 1A. Accordingly, step 704 may comprise polarizing the scattered light and detecting the polarized scattered light. The polarized scattered light may be polarized in a direction substantially perpendicular to the scattering plane associated with the scattered light.

At step 706, first data indicative of a measured scattering spectrum associated with the biofluid sample is generated using the detected scattered light. The first data may include a first array of numeric values representing wavelengths within the spectrum of interest, and a second array of numeric values representing the amplitude of the scattered light at the wavelengths defined in the first array. In some embodiments, the first data may be integrated, for example for ten seconds. In some such embodiments, step 708 is performed based on the integrated first data. In some embodiments, step 706 may be performed using processor 124 of FIG. 1A.

At step 708, it may be identified whether at least one bacterial species is present in the biofluid sample using the first data. In some embodiments, identifying whether at least one bacterial species is present in the biofluid sample may comprise determining the relative concentration of one bacterial species with respect to other bacterial species. In some embodiments, step 708 comprises (i) obtaining second data indicative of a plurality of reference scattering spectra (e.g., spectral markers), each reference scattering spectrum being associated with a respective one of the bacterial species; (ii) generating third data indicative of a linear combination of the reference scattering spectra, the linear combination comprising a plurality of unknown coefficients representing respective concentrations for the bacterial species in the biofluid sample; and (iii) determining the unknown coefficients using the first data and the third data (e.g., by generating an equation based on a comparison of the first data with the third data). In some embodiments, determining the unknown coefficients comprises applying a linear minimization approach to the equation.

The second data may include multiple data sets $S_i(\lambda)$, each data set including a first array of numeric values representing wavelengths within the spectrum of interest, and a second array of numeric values representing the amplitude of the reference scattered light associated with a particular bacterial species at the wavelengths defined in the first array. The reference spectra may be obtained using the calibration techniques described herein. The third data may include a first array of numeric values representing wavelengths within the spectrum of interest, and a second array of numeric values representing the quantity $$\sum_{i=1}^{N} c_i S_i(\lambda).$$

In some embodiments, step 708 may be performed using processor 124 of FIG. 1A. Optionally, at step 709, Rayleigh correction of the first data is performed.

Having thus described several aspects of at least one embodiment of this technology, it is to be appreciated that various alterations, modifications, and improvements will readily occur to those skilled in the art. Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The terms "program" or "software" are used herein in a generic sense to refer to any type of computer code or set of processor-executable instructions that can be employed to program a computer or other processor to implement various aspects of embodiments as described herein. Additionally, in some embodiments, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Also, various inventive concepts may be embodied as one or more processes, of which examples have been provided including with reference to FIG. 7. The steps performed as part of each method may be ordered in any suitable way. Accordingly, embodiments may be constructed in which steps are performed in an order different than illustrated, which may include performing some steps simultaneously, even though shown as sequential steps in illustrative embodiments.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Unless otherwise specified, the terms "approximately," "substantially" and "about" may be used to mean within ±10% of a target value in some embodiments. The terms "approximately," "substantially" and "about" may include the target value.

What is claimed is:

1. A method for identifying bacterial species in a biofluid sample, comprising:

illuminating the biofluid sample with input light;

detecting scattered light produced by the biofluid sample in response to the illuminating;

generating first data indicative of a measured scattering spectrum associated with the biofluid sample using the detected scattered light; and identifying whether at least one of the bacterial species is present in the biofluid sample using the first data, wherein identifying whether at least one of the bacterial species is present in the biofluid sample comprises:

obtaining second data indicative of a plurality of reference scattering spectra, each reference scattering spectrum being associated with a respective one of the bacterial species;

generating third data indicative of a linear combination of the reference scattering spectra, the linear combination comprising a plurality of unknown coefficients representing respective concentrations for the bacterial species in the biofluid sample; and determining the unknown coefficients using the first data and the third data.

2. The method of claim 1, wherein determining the unknown coefficients comprises generating an equation based on a comparison of the first data with the third data.

3. The method of claim 2, wherein determining the unknown coefficients comprises applying a linear minimization approach to the equation.

4. The method of claim 1, wherein identifying whether at least one of the bacterial species is present in the biofluid sample further comprises performing Rayleigh correction of the first data.

5. The method of claim 1, further comprising integrating the first data, wherein identifying whether at least one of the bacterial species is present in the biofluid sample further comprises identifying whether at least one of the bacterial species is present in the biofluid sample using the integrated first data.

6. The method of claim 1, wherein:

illuminating the biofluid sample with the input light comprises illuminating a blood sample with the input light; and detecting the scattered light scattered by the biofluid sample in response to the illuminating comprises detecting the scattered light produced by the blood sample in response to the illuminating.

7. The method of claim 1, wherein illuminating the biofluid sample with the input light comprises illuminating the biofluid sample with polarized input light.

8. The method of claim 7, wherein the polarized input light is polarized in a direction substantially perpendicular to a scattering plane associated with the scattered light.

9. The method of claim 1, wherein detecting the scattered light produced by the biofluid sample comprises polarizing the scattered light and detecting the polarized scattered light.

10. The method of claim 9, wherein polarizing the scattered light comprises polarizing the scattered light in a direction substantially perpendicular to a scattering plane associated with the scattered light.

11. The method of claim 1, wherein identifying whether at least one of the bacterial species is present in the biofluid sample comprises identifying whether at least one of a *Pseudomonas aeruginosa*, an *Escherichia coli*, a *Klebsiella pneumoniae*, a *Staphylococcus aureus*, a *Streptococcus pneumoniae*, a *Listeria monocytogenes*, a *Staphylococcus epidermidis*, a *Staphylococcus haemolyticus*, a *Neisseria meningitidis*, a *Haemophilus influenzae*, and a *Proteus mirabilis* is present in the biofluid sample.

12. The method of claim 1, further comprising, prior to illuminating the biofluid sample with the input light, lysing red blood cells from the biofluid sample.

13. The method of claim 12, wherein the lysing the red blood cells from the biofluid sample comprises mixing the biofluid sample with water.

14. The method of claim 1, wherein identifying whether at least one bacterial species is present in the biofluid sample further comprises determining a relative concentration of the at least one bacterial species with respect to other bacterial species.

15. A system for identifying bacterial species in a biofluid sample, comprising:

a light source;

a spectrograph and a photosensitive detector;

first and second polarizers, the first polarizer being disposed on a first optical path formed between the light source and the biofluid sample and the second polarizer being disposed on a second optical path formed between the biofluid sample and the spectrograph; and a processor coupled to the photosensitive detector and configured to:

generate first data indicative of a measured scattering spectrum associated with the biofluid sample; and identify whether at least one of the bacterial species is present in the biofluid sample using the first data, wherein the processor is configured to identify whether at least one of the bacterial species is present in the biofluid sample by:

obtaining second data indicative of a plurality of reference scattering spectra, each reference scattering spectrum being associated with a respective one of the bacterial species;

generating third data indicative of a linear combination of the reference scattering spectra, the linear combination comprising a plurality of unknown coefficients representing respective concentrations for the bacterial species in the biofluid sample; and determining the unknown coefficients using the first data and the third data.

16. The system of claim 15, wherein the processor is configured to determine the unknown coefficients by generating an equation based on a comparison of the first data with the third data.

17. The system of claim 15, wherein identifying whether at least one of the bacterial species is present in the biofluid sample further comprises performing Rayleigh correction of the first data.

18. The system of claim 15, wherein:

the first polarizer has a polarization axis substantially perpendicular to a scattering plane associated with scattered light produced by the biofluid sample in response to illumination by the light source, and the second polarizer has a polarization axis substantially perpendicular to the scattering plane.

* * * * *